United States Patent [19]

Robinson

[11] Patent Number: 5,015,585
[45] Date of Patent: May 14, 1991

[54] METHOD AND APPARATUS FOR CULTURING AND DIFFUSIVELY OXYGENATING CELLS ON ISOTROPIC MEMBRANES

[76] Inventor: James R. Robinson, 3326 Dyer Rd., Livermore, Calif. 94550

[21] Appl. No.: 159,015

[22] Filed: Feb. 23, 1988

[51] Int. Cl.$^5$ .......................... C21N 5/00; C12M 3/04
[52] U.S. Cl. .................. 435/240.242; 435/240.241; 435/284; 435/285; 435/818; 210/636
[58] Field of Search .................. 422/101, 48, 240; 435/240.2, 41, 240.23, 240.25, 240.241, 240.242, 284, 285, 286, 288, 311, 818; 210/321.6, 321.64, 321.79, 321.8, 500.22, 321.89, 500.23, 636

[56] References Cited

U.S. PATENT DOCUMENTS

| | | | |
|---|---|---|---|
| 3,883,393 | 5/1975 | Knazek et al. | |
| 4,024,020 | 5/1977 | Weiss et al. | 435/240.23 |
| 4,220,725 | 9/1980 | Knazek et al. | 435/285 |
| 4,225,671 | 9/1980 | Puchinger et al. | 35/285 |
| 4,440,853 | 4/1984 | Michaels et al. | 435/284 |
| 4,442,206 | 4/1984 | Michaels et al. | 435/284 |
| 4,647,380 | 3/1987 | Dasgupta | 210/638 |
| 4,647,539 | 3/1987 | Bach | 435/284 |
| 4,661,458 | 4/1987 | Berry et al. | 435/311 |

FOREIGN PATENT DOCUMENTS 8401959  5/1984  PCT Int'l Appl. .................. 435/285

OTHER PUBLICATIONS

Karel et al., "The Immobilization of Whole Cells: Engineering Principles", Chemical Engineering Science, vol. 40, pp. 1321-1354 (1985).
Karel et al., "Protein Synthesis and Degradation in Immobilized Cell Reactors", 78th Annual AICHE Meeting, Chicago, Il. (11/1985), pp. 1-11.
Robertson et al., "Dual Aerobic Hollow-Fiber Bioreactor for Cultivation of Streptomyces Aureotaciens" Biotechnology and Bioengineering, vol. 27(1985), pp. 1012-1020.
Libicki et al., "The Effective Dissusive Permeability of a Non-Reacting Solute in Microbial Cell Aggregates", 11/86.

Primary Examiner—Christine Nucker
Assistant Examiner—William H. Beisner
Attorney, Agent, or Firm—Longacre & White

[57] ABSTRACT

A dual hollow fiber bioreactor comprised of homopolymer construction and a method of using same. The bioreactor being created by thermal bonding incorporating a heat sink so as to preserve the structural integrity of the bioreactor during initial construction and in subsequent treatments during sterilization processes.

3 Claims, 1 Drawing Sheet

METHOD AND APPARATUS FOR CULTURING AND DIFFUSIVELY OXYGENATING CELLS ON ISOTROPIC MEMBRANES

FIELD OF THE INVENTION

The present invention is directed towards a method and apparatus for culturing cells. More particularly, the present method and apparatus are directed towards the culturing of cells which are immobilized in an annular chamber between two concentrically related tubular membranes.

BACKGROUND OF THE INVENTION

Several prior art cell culturing bioreactors have been disclosed. Examples are found in U.S. Pat. Nos. 4,647,539, 4,603,109, 4,391,912, 4,317,886, 4,242,460, 4,242,459, 4,228,243, and 4,220,725. While these prior art bioreactors permit the culturing of cells, they represent a combination of compromise cell culturing conditions owing to their configuration and material composition. Particularly, the geometric configuration of the cell culturing chamber leads to the circumstance where cells exist in regions where insufficient nutrients are present. This circumstance is predicated on the fact that the rate of consumption of the growth limiting nutrient required for culturing the cells exceeded the rate of diffusion through the cell matrix of the growth limiting nutrient. As a result, the growth limiting nutrient in some cases does not reach certain areas of the cell culturing chamber.

Other drawbacks relating to the prior art bioreactors relate to their construction materials. Particularly, the prior art bioreactors are conventionally constructed of silicone, glass, rubber, and polypropylene or other polymer. As such, each of these elements of separate materials must be adhesively bonded together. Owing to the fact that the materials are chemically dissimilar, the adhesive bonding is limited only to a mechanical type bond between the distinct bioreactor elements. As a result, repeated sterilization of the bioreactors leads to the degradation of their structural integrity and consequent failure. Failure, of course, being an undesirable characteristic in a relatively expensive piece of laboratory equipment.

The prior art attempts to solve the geometric isolation of certain cells within a culturing chamber have involved the creation of dual hollow fiber bioreactors. This construction involves placing a hollow fiber tube concentrically within another length of hollow fiber and immobilizing the cells in the annular gap existing between the concentrically related fibers. The limiting aspect of this configuration has been that either of one of the fibers has been made permeable to fluid nutrient constituents and the other fiber being permeable to gas nutrient constituents rather than a combination thereof.

The prior art has been unable to successfully create a dual hollow fiber reactor wherein both the inner and outer tubes are comprised of the same materials and therefore have the same permeability to the most desirable nutrient constituents. A typical construction of such a prior art bioreactor has included a polypropylene outer hollow fiber with a silicone tubule inserted concentrically therein or the reverse, that is, a silicone outer fiber with a polypropylene inner fiber. The remaining elements of the bioreactor comprising rubber plugs and a glass outer shell.

Although thee prior art solution discussed above more nearly attempted to create the ideal geometric cell culturing chamber in terms of distance from the nutrient source, i.e., the membrane, the construction materials of the prior art bioreactors limited the usefulness of the reactors to replicate cell growth conditions in animals and/or humans. Extensive research has determined that in the human body cells rarely exist beyond a distance of 100 microns from a nutrient capillary. As such, researchers have attempted to replicate this configuration with man-made materials. However, the stumbling block has been not only achieving the cell/nutrient source distance separation but also achieving satisfactory nutrient supplies from all sides of the cell. That is, the prior bioreactors have only been able to supply gaseous nutrients from one side and fluidized nutrients from the other. The situation of having fluidized nutrients from both sides has not been successfully achieved.

Additionally, the prior art bioreactors have consistently produced large populations of dead cells in their culturing chambers. This phenomena exists because the cells closest to the nutrient membrane push cells which are spaced away from the membrane further away from the membrane. Once the separation exceeds the diffusive capacity of the nutrients, the cell dies. Once a cell dies, it becomes more easily compressible because it can no longer exert growth pressure of its own against surrounding cells. As a result, growing cells located closer to the nutrient source are able to continually push those cells which are spaced more remotely further into their respective remote area. Eventually, the growing cells generate a band of dead cells which is continually crushed by the growing pressure of the living cells. Since the dead cells compact more easily into solids than do the living cells, the population of compacted dead cells can equal or exceed the population of living cells.

Hence, the prior art bioreactors although useful for culturing cells also include severe limitations to their utility because of both their ability to create two cell populations within their culturing chambers and also, owing to their distinct component part construction, limited reusability thereof. The present invention seeks to avoid the problems associated with prior art bioreactors through the combination of dual hollow fiber configuration and homopolymer material construction.

SUMMARY OF THE INVENTION

A bioreactor according to the present invention comprises a pair of concentrically related hollow fibers incorporated within a bioreactor unit constructed of a single polymer. The construction of the bioreactor is accomplished by a method of thermal bonding so that there do not exist any adhesive bonds between separate elements of the reactor which may break down because of repeated sterilizations of the bioreactor unit.

Additionally, the respective diameters of the concentrically related hollow fibers are judiciously chosen so as to create an annular cell culturing chamber which results in little or no limitations to nutrient (oxygen) access to the growing cells, the annular spacing between the concentrically related hollow fibers being on the order of 200 microns.

The method according to the present invention uses a bioreactor of homopolymer construction and concentric geometric configuration as described above so as to create a cell population consisting primarily of viable and productive cells. The method includes the convective passage of fluidized nutrients over the sides of respective concentrically related hollow fiber membranes so as to nourish the cells immobilized in the annular cavity between the hollow fibers.

DETAILED DESCRIPTION OF THE PREFERRED EMBODIMENT

With reference to drawing FIGS. 1 and 2, the method and apparatus for cell culturing according to the present invention will now be described.

Figure 1:
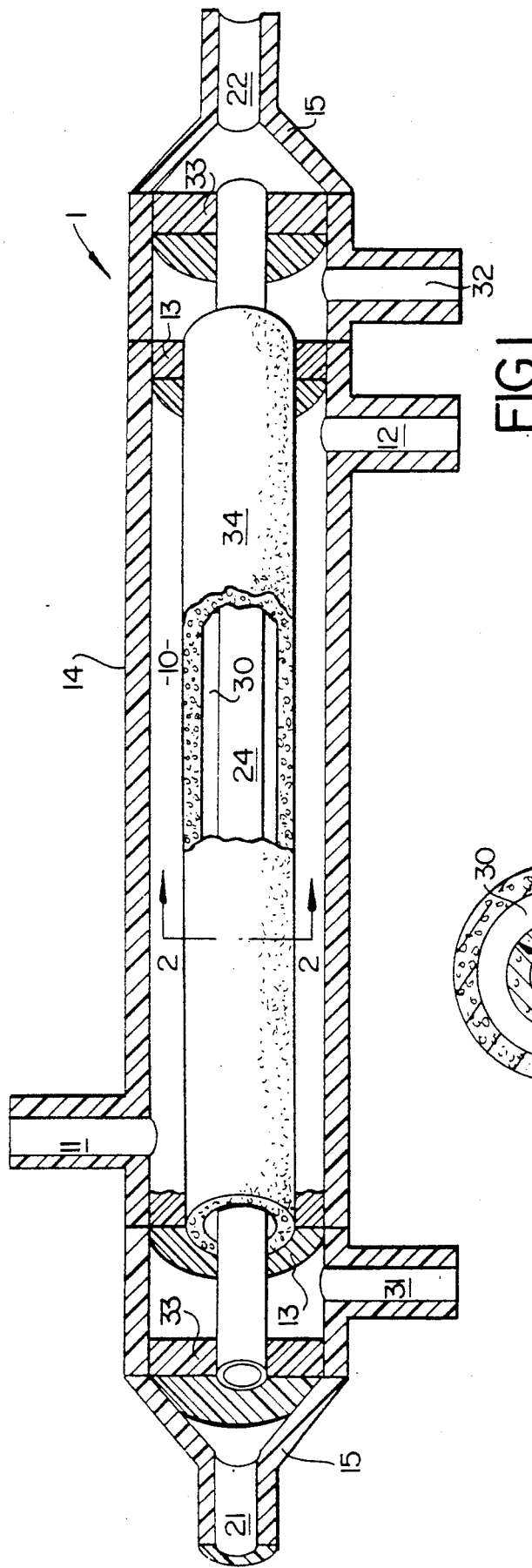
FIG. 1 is a partial sectional view of a bioreactor according to the present invention.

FIG. 1 discloses a bioreactor according to the present invention in its most simplistic form. That is, the bioreactor of FIG. 1 includes only a single pair of concentrically related fibers contained 24, 34 within the module shell 14. In commercial embodiments of the present bioreactor, there would exist several dozen pairs of concentrically related hollow fibers within a single module.

A bioreactor 1 according to the present invention is of known physical configuration. Extending through the entire length of the bioreactor 1 is the intracapillary microporous isotropic hollow fiber 24. This hollow fiber 24 is comprised of a polypropylene membrane of approximately 0.2 millimeters thickness. The pore size of this membrane is in the range of 0.2 microns. The inside diameter of the intracapillary hollow fiber 24 being approximately 0.6 millimeters and the outside diameter being approximately 0.8 millimeters. The intracapillary hollow fiber 24 carries nutrients in a convective manner through the length of the bioreactor from the intracapillary nutrient port 21 to exit port 22 at the opposite end of the bioreactor 1. The intracapillary hollow fiber 24 is sealed at each end thereof to the module shell 14 by the intracapillary end potting members 33. These potting members 33 separate and isolate the flow of nutrients entering through port 21 and exiting through port 22 from the remaining volume of the bioreactor.

Concentrically surrounding the intracapillary hollow fiber 24 is extracapillary microporous isotropic hollow fiber 34. Fiber 34 is comprised of the same polypropylene membrane as is hollow fiber 24. The larger hollow fiber 34 has an inside diameter of approximately 1.2 millimeters and an outside diameter of approximately 1.8 millimeters. The inside diameter of fiber 34 and the outside diameter of fiber 24 are selected such that the spacing between them is on the order of 0.2 millimeters in the radial direction. This spacing requirement will be discussed in greater detail below.

The extracapillary hollow fiber 34 is also sealed at each end to module shell 14 by extracapillary end pottings 13. The end potting 13 seals hollow fiber 34 to the surrounding module shell 14 so as to isolate nutrient chamber 10 from the remaining volume of the bioreactor. Nutrient chamber 10 is fed by extracapillary nutrient port 11 and is exhausted by extracapillary exhaust port 12.

The annular space defined between the hollow fibers 34 and 24 is cell culturing chamber 30. This chamber is defined between the hollow fibers and also extends to include the sections of the module shell 14 which are isolated between the respective end pottings of hollow fibers 34 and 24. Culturing chamber 30 is supplied with cells through inoculation port 31 and is exhausted through cell exhaust port 32.

Covering the ends of the reactor module shell 14 are end cap manifolds 15. These manifolds serve to enable the connection of conventional tubing and hardware through which to feed the fine intracapillary tubing 24.

Figure 2:
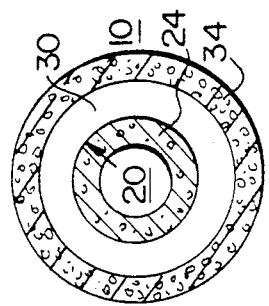
FIG. 2 is a cross sectional end view along section line 2—2 of FIG. 1.

FIG. 2 illustrates the spatial relationship between the concentrically related hollow fibers 24 and 34. Particularly, the width of the annular space between the hollow fibers is approximately 0.2 millimeters or 200 microns. This spacing is rather critical for the successful growth of certain mammalian cells.

As mentioned previously, researchers have been trying to replicate the reproduction of cells as performed by the human body. Research has indicated that cells in the human body exist at a maximum distance of 100 microns from their nearest source of nutrients, i.e., a capillary. Additional research performed to determine the reasons behind this distance relationship have confirmed that for a wide range of cell types and nutrient types, the distance of 100 microns yields viable and productive mammalian cells.

The bioreactor according to the present invention attempts to mimic the human body in two ways. Firstly, the bioreactor places the culturing cells at a maximum distance of 100 microns from their nutrient source, i.e., the membrane. Secondly, a bioreactor according to the present invention permits fluidized nutrient sources to pass through membranes located on either side of the cultured cell so as to provide idealized nutrients from both sides of the cell.

The 100 micron distance is determined by the diffusion gradient of the nutrients as they pass from the membrane into the cell structure located nearest the membrane. As the nutrient passes into the cell layer the nutrient is consumed by the cells through which it is diffusing. Beyond a certain distance from the nutrient source, the nutrient can no longer diffuse since it has been completely consumed by the cell layers through which it has been diffusing. The rate of consumption of the growth limiting nutrient of growing cells can be considered as a constant K. This rate of consumption must be less than or equal to the diffusive rate of permeability De of the growth limiting nutrient for the cells to live. The equation $De-K \geq 0$ must govern the entire cell culturing chamber for viable and productive cells to exist throughout.

The geometric configuration of the bioreactor according to the present invention permits a cell to not exceed a distance of 100 microns from the nearest fluidized nutrient source. That is, with the spacing between the hollow fibers limited to 200 microns, the maximum distance which a cell can be placed from a fluidized nutrient source is 100 microns.

An important element of the present bioreactor is its homopolymer construction. That is, the module shell, hollow fibers, end potting, and manifolds are all comprised of a chemically similar polymer. The entire module is constructed of homopolymer selected for example from a variety of materials such as polypropylene, nylon, polysulfone, etc. A particularly preferable homopolymer is one composed of polypropylene. The object being to achieve components which are either all negatively charged, positively charged or noncharged and exist with the same coefficient of expansion. In this manner, successive treatments of the bioreactor within an autoclave between culturing experiments and/or production will not degrade the quality or integrity of the bioreactor owing to absence of adhesive bonds in the construction of the bioreactor.

To accomplish this construction, the bioreactor must be assembled using a thermal bonding technique. That is, the component parts of the bioreactor must chemically bond to one another without the aid of a foreign adhesive. The bond between the components must exist beyond a mere surface attraction, i.e., a much stronger bond such as hydrogen bonding between adjacent chains within the homopolymer component parts.

To achieve this construction with the rather small diameter membrane tubes, a method of thermal bonding using a heat sink must be employed. That is, when bonding is being attempted between one of the hollow fibers and a potting which subtends the hollow fibers, the hollow fiber must first have its end threaded onto a steel rod so as to maintain its shape during the heating and welding process.

A typical bonding process between one of the hollow membrane fibers and an end potting portion will now be described. The hollow membrane fibers are cut to an appropriate length and suitably trimmed and cleaned so as to be completely free from foreign substances (finger prints, oils, dust). A steel rod is then cut to a length which slightly exceeds the overall length of the hollow fiber to be attached. The steel rod is machined on each end so as to remove all burs and other imperfections which might impair the uniformity of a hollow fiber through which the steel rod must thread. The steel rod is also appropriately cleaned so as to remove all foreign matter and is then coated with PTFE so as to aid in threading it through the hollow fiber membrane.

Once the hollow fibers have been threaded through with the respective steel rods, the end potting mold can be prepared. Beads of the appropriate polymer are heated within the end potting mold so as to take the shape of the end potting shape desired. Simultaneously, an end of the rod and fiber combination which is to be bonded to the end potting is brought up to bonding temperature. This heating step includes heating an end of the steel rod hollow fiber combination. When the polymer material within the mold and the hollow fiber rod combination have been raised to a temperature suitable for bonding, i.e., 190° C. and 140° C. respectively (depending on the selection of polymer), the rod and fiber combination with the surrounding shell portion is inserted into the mold containing the end potting material. The potting material being sufficiently liquid to adequately surround the inserted tube and rod combination. The entire combination of hollow fiber, rod, shell, and end potting are then quenched in a cooling solution, i.e., water.

When the combination is suitably cooled and withdrawn from the end potting mold, the steel rods are driven through the end potting so as to create a through passage through the end potting member corresponding to the hollow fiber membrane which surrounds the rod. When a short section of the rod has been drawn through the end potting piece, the rod is suitably trimmed and the rod eventually withdrawn, subsequent to the creation of the opposite end potting member, so as to leave only the hollow membrane tube and end potting combination for subsequent assembly into the completed bioreactor.

This technique of thermal bonding permits a combination of solid end potting units with membrane type fibers in a suitably welded combination. The use of the steel rod enables the porous membrane to maintain its shape and integrity while being bonded to a much more dense polymer member.

In the construction of the present bioreactor, the outer hollow fiber, or extracapillary hollow fiber is first thermally bonded to the extracapillary end potting 13 and outer shell portion. An additional shell extension is then thermally bonded to the shell/end potting/hollow fiber combination. The third bonding step then involves bonding the intracapillary tube 24 to the intracapillary end potting 33. Once these thermal bonding steps have been completed, the module shell construction is completed by thermally bonding the separate end cap manifolds 15 to each end of the bioreactor module 1.

In operation, the bioreactor according to the present invention is connected in the following manner. Nutrient inlet ports 11 and 21 are connected to suitable supplies of oxygenated nutrients which are then pumped through the respective nutrient passages in the associated intracapillary hollow fiber 24 and nutrient chamber 10. The cell inoculation port 31 is connected to a suitable supply of cell containing fluid so that the cells may enter and pack cell chamber 30. An example of a 3 ml capacity bioreactor is listed below.

| EXAMPLE | |
| --- | --- |
| CELL CHAMBER GROWTH VOLUME | 3 ml |
| CELL TYPE | MURINE/MURINE HYBRIDOMA |
| TOTAL CELL POPULATION | $5-6 \times 10^8$ |
| CELL DENSITY | $1.5-2.0 \times 10^8$/ml |
| INNOCULUM | $10^7$ CELLS (reaches maximum density in 4–5 days) $10^6$ CELLS (reaches maximum density in 7–8 days) |
| CELL DOUBLING RATE | LOG PHASE, 1.3–1.4 TIMES/DAY STATIONARY PHASE <0.05 TIMES/DAY |
| MEDIUM TYPE | MODIFIED DME, SERUM FREE |
| MEDIUM RECIRCULATION RATE | 40–50 ml/min |
| MEDIUM VOLUME | 200–1000 ml |
| SECRETED ANTIBODY | 1 gG |
| ANTIBODY PRODUCTIVITY | 7.5 mg/day (pure, isolated from 100 ml spent media) |

NOTE:
STATIONARY PHASE MAINTAINED FOR 20 DAYS MINIMUM WITHOUT CHANGES IN UPTAKE RATE OF GLUCOSE, GLUTAMINE, OXYGEN, ETC., AND NO LIMITING NUTRIENTS.

The particular choice of nutrients, cells and related operational pressures are, of course, related to the particular desires of the bioreactor operator. These desires will be based on the nature of the cells to be cultured in other cell culturing parameters.

What is claimed is:

1. A method for culturing cells on isotropic polymer membranes, comprising the steps of:
    immobilizing said cells in a cell growth chamber said chamber having at least two opposite sides thereof defined by a thickness of isotropic polymer membrane, and being bounded on all remaining sides by jacket means each thickness of said membrane having first and second surfaces, each of said first surfaces being directed inwardly with respect to said chamber and being separated by no more than 200 microns, and wherein said chamber defined by said membranes and said jacket means is constructed of the same polymer material, and passing nutrient fluid across said second surfaces of said membrane, and diffusing said fluid through said membranes and into said growth chamber.

2. Apparatus for culturing cells on isotropic membranes comprising:

a first tubular element having first and second ends and having a wall, said wall comprising an isotropic polymer membrane having an inner surface and an outer surface, and a second tubular element having first and second ends and having a wall, said wall comprising an isotropic polymer membrane having an inner surface and an outer surface, said second tubular element being sized so as to telescopically encompass an intermediate length of said first tubular element, and jacket means comprising a non-porous polymer for enveloping said first and second tubular elements, wherein said first and second ends of said second tubular element sealingly engage said jacket means around the entire circumference thereof, so that said first and second ends of said second tubular element, in combination with said outer surface of said second tubular element, and said jacket means form boundaries of a first chamber, said first chamber having an inlet port and an outlet port located therein, and wherein said first and second ends of said first tubular element also sealingly engage said jacket means around the entire circumference thereof so that said first and second ends of each of said tubular elements, said inner surface of said second tubular element, said outer surface of said first tubular element, and said jacket means form boundaries of a second chamber, said second chamber having an inlet port and an outlet port located therein, and said second chamber is shaped such that he distance from said outer surface of said first tubular element to said inner surface of said second tubular element is no more than 200 microns, so that when cells are inserted into said second chamber through said inlet port and fluidized nutrients are passed through said first chamber and said first tubular element, nutrients pass through said respective walls of said first and second tubular elements to said cells contained in said second chamber, and wherein, said apparatus is constructed entirely of the sample polymer material as the isotropic polymer membranes.

3. An apparatus according to claim 2, wherein said apparatus is made using thermal bonding to secure the separate elements thereof together.

* * * * *